United States Patent [19]

Harley et al.

[11] Patent Number: 4,604,242

[45] Date of Patent: Aug. 5, 1986

[54] PREPARATION OF DIALIPHATIC, DIALICYCLIC, OR DI(ARYL-SUBSTITUTED ALIPHATIC) CARBONATES

[75] Inventors: A. Dale Harley; Jerald L. Curnutt; David T. Doughty, all of Midland, Mich.

[73] Assignee: The Dow Chemical Company, Midland, Mich.

[21] Appl. No.: 590,596

[22] Filed: Mar. 19, 1984

[51] Int. Cl.$^4$ .............................................. C07C 68/00
[52] U.S. Cl. .................................... 558/260; 558/274; 558/277; 558/270
[58] Field of Search ............................................ 260/463

[56] References Cited

U.S. PATENT DOCUMENTS 4,136,097  1/1979  Maryanoff ........................ 260/326.2
4,360,477  11/1982 Hallgren ............................ 260/463
4,361,519  11/1982 Hallgren ............................ 260/463

OTHER PUBLICATIONS

Bertrand et al., *Inorganic Chemistry*, vol. 4, No. 11, pp. 1657–1659, Nov. 1965.
Saegusa et al., *J. Org. Chem.*, vol. 35, No. 9, p. 2976 (1970).

*Primary Examiner*—Robert Gerstl
*Assistant Examiner*—Stephen M. Kapner

[57] ABSTRACT

This invention is a process for the preparation of a symmetrical or unsymmetrical dihydrocarbyl carbonate which comprises contacting an aliphatic, cycloaliphatic or di(aryl-substituted aliphatic) alcohol or mixtures thereof with carbon monoxide and oxygen in the presence of a catalytic amount of bis((2,4-pentanedianato)-copper (II) methoxide) and a cocatalytic amount of a basic nitrogen-containing coordination compound under conditions such that a symmetrical or unsymmetrical dihydrocarbyl carbonate is prepared.

8 Claims, No Drawings

PREPARATION OF DIALIPHATIC, DIALICYCLIC, OR DI(ARYL-SUBSTITUTED ALIPHATIC) CARBONATES

BACKGROUND OF THE INVENTION

This invention relates to a process for the preparation of dialiphatic, dialicyclic, or di(aryl-substituted aliphatic)carbonates. More specifically, the process relates to a process wherein dialiphatic, dialicyclic, or di(aryl-substituted aliphatic)alcohols are oxidatively carbonylated so as to prepare such carbonates.

The carbonates produced by this invention are well-known and are useful as synthetic lubricants, solvents, and chemical intermediates in the preparation of pharmaceutically active compounds and in the preparation of polymeric derivatives, for example, clear plastics.

Carbonates are typically produced by contacting phosgene with the appropriate alcohol. See Drake et al., *J. Am. Chem. Soc.*, 52, 3720 (1960) and U.S. Pat. No. 2,379,250. The hydrogen chloride that is produced by this process is not easily eliminated and leads to the production of chlorine-containing products. Attempts to neutralize the hydrogen chloride, e.g., with an acid acceptor, have led to processing difficulties. Moreover, when secondary alcohols are employed, the competing reaction involving alkyl chloride formation is serious and necessitates the use of an acid acceptor.

Frevel et al., U.S. Pat. No. 3,642,858, disclose that carbonates can be prepared by reacting a cyclic alkylene carbonate with a nontertiary hydroxy-containing compound in the presence of a catalytic amount of an alkali metal.

Gaenzler et al., U.S. Pat. No. 3,952,045, disclose a method for preparing carbonates which comprises reacting an alcohol, with carbon monoxide and oxygen, in the presence of a catalyst comprising a copper salt, chloride or bromide, and an organic phosphorus compound.

Romano et al., U.S. Pat. No. 4,218,391, disclose the preparation of carbonates by reacting an alcohol with oxygen and carbon monoxide in the presence of a catalyst which is a salt of a metal belonging to Groups IB, IIB, and VIII of the Periodic Table; the least possible number of inorganic anions is desirable in order to reduce the acidity of the environment as far as possible. The salts of monovalent copper are preferred.

Stammann et al., U.S. Pat. No. 4,370,275, disclose a process for the preparation of carbonates wherein an alcohol is reacted with a mixture of molecular oxygen and carbon monoxide in the liquid phase in the presence of a catalyst containing copper, chemically bonded oxygen, chemically bonded halogen and at least one nitrogen base.

Cipriani et al., U.S. Pat. No. 3,980,690, disclose the preparation of a carbonate which comprises reacting an alcohol with oxygen and carbon monoxide in the presence of a catalyst in the heterogeneous phase by introducing the reactants into a reactor charged with a catalyst such as the complex of a system formed by copper and 4-vinylpyridine, causing the reactants to flow over the catalyst, and then withdrawing the products of the reaction and unconsumed reactants from the reactor. It is taught that in order to obtain the catalyst described in the invention, use may be made of salts of metals belonging to the IB, II and VIII Groups of the Periodic system. For instance, salts of metals selected from among copper, silver, gold, zinc, cadmium, mercury, iron and nickel. The most suitable anions, to which the metal ion is bound, are selected from halides, CN-, ClO$_4$- or complex ions of the BF$_4$- type and the like.

Perrotti et al., U.S. Pat. No. 3,846,468, describe a process for the preparation of carbonates which comprises reacting an alcohol with oxygen and carbon monoxide in the presence of a catalyst which is copper complexed with an inorganic molecule. The catalyst disclosed generally corresponds to the formula $MX_nL_m$ wherein M is a metal of IB, IIB or Group VIII of the Periodic system, preferably copper, silver, gold, zinc, cadmium, mercury, iron, cobalt, nickel, that is, metals able to exist in two different valence conditions by means of redox reactions; X is an anion; and L is a neutral ligand. With the more suitable anions being halide ions, cyanate ions, hypochlorate ions, and complex anions of BF$_4$- and the like. The ligands are selected from the group consisting of organic bases such as pyridine, dipyridyl, imidazole, phenanthroline, alkyl or aryl phosphines, dimethyl sulfoxide, dimethylformamide, quinuclidine, carbon monoxide, suitable ligands are also the nitriles such as acetonitrile, cyanobenzene, and the bidentate ligands such as malonitrile, succinodinitrile, adiponitrile and the like.

Hallgren et al., U.S. Pat. No. 4,361,519, disclose a process for the preparation of carbonates which comprises contacting an alcohol, carbon monoxide, a Bronsted base, a Group VIIIB element, oxygen and a redox cocatalyst.

Hallgren et al., U.S. Pat. No. 4,360,477, disclose the preparation of alkyl carbonates by carbonylation of alkanols with carbon monoxide and oxygen at elevated temperatures in the presence of certain copper salts.

The processes described hereinbefore generally demonstrate slow kinetics and have poor selectivity towards the desired carbonates under conditions which are suitable for commercial processes. Furthermore, many of the processes result in the presence of metal salts, such as copper halide salts, being present during the process. Such metals salts are generally corrosive and create significant problems in processing.

What is needed is a process for the preparation of carbonates wherein the rate of reaction is reasonable, the selectivity towards carbonates is high and there are no corrosive elements present so as to create significant problems in processing.

SUMMARY OF THE INVENTION

This invention is a process for the preparation of a symmetrical or unsymmetrical dihydrocarbyl carbonate which comprises contacting an aliphatic, cycloaliphatic or di(aryl-substituted aliphatic)alcohol or mixtures thereof with carbon monoxide and oxygen in the presence of a catalytic amount of bis((2,4-pentanedianato)-copper (II) methoxide) and a cocatalytic amount of a basic nitrogen-containing coordination compound under conditions such that a symmetrical or unsymmetrical dihydrocarbyl carbonate is prepared.

The process of this invention results in a reasonable rate of formation of the desired products. Furthermore, the selectivity of the process of this invention is much higher than such hereinbefore discussed processes. A significant advantage of the process of this invention is that no corrosive metal salts are produced or are present during the process, so as to create processing problems.

DETAILED DESCRIPTION OF THE INVENTION

In general, the alcohols useful in this invention are those which will undergo carbonylation under the reaction conditions so as to form carbonates. These alcohols include aliphatic alcohols, cycloaliphatic alcohols, and aryl-substituted aliphatic alcohols. Desirable alcohols useful in this invention include those which correspond to $R^1OH$ wherein $R^1$ is a $C_{1-20}$ aliphatic, $C_{3-20}$ cycloaliphatic, or $C_{7-20}$ aryl-substituted aliphatic moiety.

Examples of alcohols which are useful in this invention include methanol, ethanol, propanol, isopropanol, butanol, sec-butanol, t-butanol, pentanol, hexanol, heptanol, octanol, nonanol, cyclopropanol, cyclobutanol, cyclopentanol, cyclohexanol, cycloheptanol, cyclooctanol, cyclononanol, benzyl alcohol, 2-phenylethanol, 3-phenylpropanol, and the like. Preferred alcohols include methanol, ethanol, propanol, butanol, pentanol, cyclopentanol, cyclohexanol, cycloheptanol, cyclooctanol, and benzyl alcohol. More preferred alcohols include methanol, ethanol, propanol, benzyl alcohol, cyclohexanol, and the like. The most preferred alcohol is methanol.

In general, the alcohol or mixture of alcohols is contacted with oxygen and carbon monoxide under carbonylation conditions so as to prepare a carbonate. In the embodiment wherein a mixture of alcohols is used, the carbonates prepared are a mixture of symmetrical and unsymmetrical carbonates. When a single alcohol is used, the product is a symmetrical carbonate. The symmetrical dihydrocarbyl carbonates are the preferred dihydrocarbyl carbonates. Preferred carbonates prepared by this invention include dialiphatic carbonates, dicycloaliphatic carbonates or di(aryl-substituted aliphatic)carbonates. Desirable carbonates prepared by this invention include those which correspond to

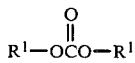

wherein $R^1$ is separately in each occurrence a $C_{1-20}$ aliphatic, $C_{3-20}$ cycloaliphatic, or $C_{7-20}$ aryl-substituted aliphatic moiety.

Examples of carbonates prepared by this invention include dimethyl carbonate, diethyl carbonate, dipropyl carbonate, dibutyl carbonate, dipentyl carbonate, dihexyl carbonate, diheptyl carbonate, dioctyl carbonate, dinonyl carbonate, dicyclopropyl carbonate, dicyclobutyl carbonate, dicyclopentyl carbonate, dicyclohexyl carbonate, dicycloheptyl carbonate, dicyclooctyl carbonate, dibenzyl carbonate, di-2-phenylethyl carbonate, and the like. Preferred carbonates prepared by this process include dimethyl carbonate, diethyl carbonate, dipropyl carbonate, dibutyl carbonate, dipentyl carbonate, dicyclopentyl carbonate, dicyclohexyl carbonate, dicycloheptyl carbonate, dicyclooctyl carbonate, and dibenzyl carbonate. The most preferred carbonate prepared by this invention is dimethyl carbonate.

The process of this invention can be illustrated by the equation

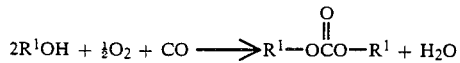

wherein $R^1$ is as defined hereinbefore.

The invention involves the use of a novel catalyst for the hereinbefore described process. The catalyst useful in this process is bis(2,4-pentanedianato)copper (II) methoxide) and corresponds to the formula

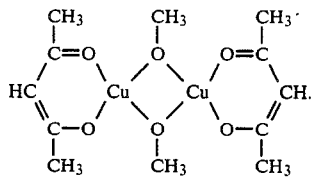

The cocatalyst in this process is any basic nitrogen-containing coordination compound. Desirable nitrogen-containing coordination compounds include ammonia, primary amines, secondary amines, heterocyclic amines, aromatic amines, organic nitriles and the oligomers of ethylenimine.

Primary amines useful in this invention include aminomethane, aminoethane, 1-aminopropane, 1-amino-1-methylethane, 1-aminobutane, 1-amino-2-methylpropane, 1-amino-1,1-dimethylethane, aminopentanes, aminohexanes, aminocyclohexane, aminoheptanes, aminooctanes, aminododecanes, aminooctadecanes, aminoeicosane, aminotriacontanes, benzylamine, chlorobenzylamine, nitrobenzylamine, 2-ethoxyethylamine, 4-carbomethoxyhexylamine, aniline, toluidine, anisidine, nitroaniline, bromoaniline, xylidines, 4-ethylaniline, and naphthylamine.

Secondary amines include dimethylamine, diethylamine, di-n-propylamine, diisopropylamine, di-n-butylamine, di-sec-butylamine, diisobutylamine, di-t-amine, dipentylamines, dihexylamines, dioctylamines, ditriacontanylamines, n-methylethylamine, n-methylpropylamine, n-methyloctadecylamine, n-ethylhexylamine, n-ethyldodecylamine, n-propyldodecylamine, diphenylamine, n-phenylnaphthylamine, n-ethylaniline, n-methyl-o-toluidine, n-methyl-p-toluidine, p-chloro-n-methylaniline, N,N'-dimethylphenylenediamine, 4-ethylaniline, 4-propylaniline, 4-butylaniline, 4-decylaniline.

Heterocyclic secondary amines include piperazine, pyrrole, imidazoline, pyrazole, 2-methylpiperadine, pyrrolidine, oxazolidine, morpholine and ethylenimine.

Aromatic nitrogen compounds include imidazole, triazole, tetrazole, pyridine, 2,4,6-trimethylpyridine, dimethylaminopyridine, benzimidazole, benzotriazole, 2-(5-aminopentyl)benzimidazole, 1,2-pentamethylenebenzimidazole. Nitriles include acetonitrile, benzonitrile, malonitrile, succinodinitrile, and adiponitrile. Preferred basic nitrogen compounds include trialkylamines, triethylenediamine, pyridine, a substituted pyridine, imidazole, piperidine, ammonia or acetonitrile.

More preferred basic nitrogen compounds are pyridine, substituted derivatives of pyridine, ammonia and acetonitrile, with pyridine being the most preferred.

The catalyst can be present in any amount which results in the hereinbefore described process proceeding at a reasonable rate with a reasonable yield. Generally, the catalyst concentration is between about 0.01 and 100 percent by weight based upon the alcohol. Preferably, the catalyst concentration is between about 0.1 and 10 percent by weight based upon the alcohol, with between about 0.1 and 1.0 percent by weight being most preferred.

Generally, the cocatalyst, which is the nitrogen-containing coordination compound, is present in a sufficient ratio to the catalyst so as to result in the process proceeding at a reasonable rate and yield. Generally the ratio of cocatalyst to catalyst is between about 1:1 and 1000:1, with between about 1:1 and 20:1 being preferred. The cocatalyst to catalyst ratio is more preferably between about 1:1 and 10:1.

The ratio of the alcohol to the oxygen is preferably between about 1:1 and 10,000:1, with between about 1:1 and 1000:1 being most preferred. The molar ratio of alcohol to carbon monoxide is preferably between about 1:1 and 10,000:1, and between about 1:1 and 1000:1 being most preferred. The ratio of oxygen to carbon monoxide is preferably between about 1:1 and 1:1000, with between about 1:1 and 1:10 being most preferred.

In general, this process is performed in an inert organic solvent or in an excess of the cycloaliphatic alcohol, aliphatic alcohol or aryl-substituted aliphatic alcohol. Desirable inert organic solvents include chlorinated hydrocarbon solvents, chlorinated aromatic hydrocarbon solvents, aliphatic hydrocarbon solvents or aromatic hydrocarbon solvents. It is most preferred to perform the process in an excess of the cycloaliphatic alcohol, aliphatic alcohol or aryl-substituted aliphatic alcohol.

This process can be performed at any temperature at which the reaction proceeds. Preferable temperatures are between about 20° C. and 200° C. with between about 80° C. and 150° C. being most preferred.

The process can be performed at any pressure at which the process proceeds. Preferable pressures are between about 1 and 200 atmospheres, with between about 10 and 50 atmospheres being most preferred.

The process of this invention preferably results in a selectivity of 75 mole percent toward the carbonate product based upon the carbon monoxide product, more preferably about 80 percent by weight. Selectivity is calculated by dividing the moles of carbonate prepared by the moles of carbonate and $CO_2$ product prepared.

This process can be run in a continuous or batch processing mode. The carbonate product can be recovered from the reaction mixture as an azeotrope with the alcohol used as a starting reactant.

SPECIFIC EMBODIMENTS

The following example is included to illustrate the invention, and does not limit the scope of the invention or the claims. All parts and percentages are by weight unless otherwise stated.

EXAMPLE

Bis(2,4-pentanedianato)copper (II) methoxide) (0.398 g, 0.105 mmole), 300 cc of methanol (237 g, 7.42 moles) and 15 cc of pyridine are added to a glass liner in a 1-liter autoclave. The reactor is sealed, pressurized to 500 lb/in$^2$ with a 4 to 1 mixture of carbon monoxide and oxygen, stirred and heated to 100° C. After two hours, gas chromatography shows the gas phase to contain 0.012 mole oxygen and 0.018 mole carbon dioxide and the liquid phase to contain 0.168 mole of dimethyl carbonate. The rate of reaction is $4 \times 10^{-3}$ moles of dimethyl carbonate/g moles copper/second, while the selectivity of dimethyl carbonate based on the carbon monoxide is 79 mole percent.

What is claimed is:

1. A process for the preparation of a symmetrical or unsymmetrical dihydrocarbyl carbonate which comprises contacting an aliphatic, cycloaliphatic or di(aryl-substituted aliphatic)alcohol or mixtures thereof with carbon monoxide and oxygen in the presence of between about 0.1 and 10 percent by weight based on the alcohol of bis((2,4-pentanedianato)copper (II) methoxide) and a cocatalytic amount of a basic nitrogen-containing coordination compound selected from the group consisting of a trialkylamine, pyridine, a substituted pyridine, imidazole, ammonia or acetonitrile, under conditions such that a symmetrical or unsymmetrical dihydrocarbyl carbonate is prepared.

2. The process of claim 1 wherein the dialiphatic, dicycloaliphatic or di(aryl-substituted aliphatic)carbonate corresponds to the formula

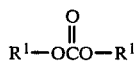

and the aliphatic, cycloaliphatic, and aryl-substituted aliphatic alcohol correspond to the formula

wherein $R^1$ is separately in each occurrence a $C_{1-20}$ aliphatic, $C_{3-20}$ cycloaliphatic or $C_{7-20}$ aryl-substituted aliphatic moiety.

3. The process of claim 2 wherein the nitrogen compound is pyridine, a substituted pyridine, ammonia or acetonitrile.

4. The process of claim 3 wherein the process is performed in a solvent which comprises excess cycloaliphatic, aliphatic or aryl-substituted aliphatic alcohol or is a chlorinated hydrocarbon solvent, an aliphatic hydrocarbon solvent or an aromatic hydrocarbon solvent.

5. The process of claim 4 wherein the mole ratio of the nitrogen-containing coordination compound and the bis((2,4-pentanedianato)copper (II) methoxide) is between about 1:1 and 1000:1.

6. The process of claim 5 wherein the alcohol is contacted with carbon monoxide in a mole ratio of 1:1 to 1:10,000.

7. The process of claim 6 wherein the temperature is between about 20° C. and 200° C.

8. The process of claim 7 wherein the reaction pressure is between 10 and 50 atmospheres.

* * * * *